(12) United States Patent
Laroche et al.

(10) Patent No.: US 10,315,132 B2
(45) Date of Patent: Jun. 11, 2019

(54) PROCESS FOR SEPERATING XYLENES BY SIMULATED COUNTER-CURRENT, TREATING A FEED INCLUDING OXYGEN-CONTAINING AROMATIC IMPURITIES OF THE PHENOL TYPE

(71) Applicant: IFP Energies nouvelles, Rueil-Malmaison (FR)

(72) Inventors: Catherine Laroche, Charly (FR); Philibert Leflaive, Mions (FR); Thierry Leflour, Paris (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 443 days.

(21) Appl. No.: 14/492,756

(22) Filed: Sep. 22, 2014

(65) Prior Publication Data
US 2015/0087878 A1    Mar. 26, 2015

(30) Foreign Application Priority Data

Sep. 20, 2013 (FR) .................................... 13/59.083

(51) Int. Cl.
*C07C 7/13* (2006.01)
*B01D 15/12* (2006.01)
*B01D 15/16* (2006.01)
*B01D 15/26* (2006.01)
*B01D 15/18* (2006.01)

(52) U.S. Cl.
CPC ....... *B01D 15/265* (2013.01); *B01D 15/1828* (2013.01); *C07C 7/13* (2013.01); *B01D 15/12* (2013.01); *B01D 15/16* (2013.01)

(58) Field of Classification Search
CPC ................................. C07C 7/135; C07C 7/12
See application file for complete search history.

(56) References Cited

U.S. PATENT DOCUMENTS

| 5,948,950 A | 9/1999 | Hotier et al. |
|---|---|---|
| 6,284,695 B1 | 9/2001 | Winter et al. |
| 6,376,734 B1 | 4/2002 | Magne-Drisch et al. |
| 2009/0326309 A1* | 12/2009 | Priegnitz ................ B01J 20/183 585/820 |
| 2009/0329309 | 12/2009 | Priegnitz et al. |
| 2012/0316375 A1* | 12/2012 | Zheng .................... C07C 2/864 585/450 |
| 2013/0006031 A1* | 1/2013 | Leflaive ............. B01D 15/1821 585/821 |
| 2013/0324780 A1* | 12/2013 | Ou .......................... C07C 7/13 585/466 |

FOREIGN PATENT DOCUMENTS

| FR | 2757507 A1 | 6/1998 |
|---|---|---|
| FR | 2795407 A1 | 12/2000 |
| FR | 2976501 A1 | 12/2012 |

OTHER PUBLICATIONS

Search Report for related French Application No. 13/59.083 dated May 16, 2014.

* cited by examiner

*Primary Examiner* — Youngsul Jeong

(74) *Attorney, Agent, or Firm* — Millen, White, Zelano & Branigan, PC

(57) ABSTRACT

The present invention describes a process for separating xylenes in simulated counter-current (simulated moving bed, SMB) for the treatment of feeds including oxygen-containing aromatic impurities of the phenol type and/or derivatives thereof, by controlled injection of water in the ingoing streams.

12 Claims, No Drawings

PROCESS FOR SEPERATING XYLENES BY SIMULATED COUNTER-CURRENT, TREATING A FEED INCLUDING OXYGEN-CONTAINING AROMATIC IMPURITIES OF THE PHENOL TYPE

FIELD OF THE INVENTION

The market for paraxylene has developed considerably, its outlets being mainly the production of terephthalic acid (TPA) obtained by oxidation of paraxylene, on which the polyester fibres used for clothing and polyethylene terephthalate (PET) resins and films are based. Paraxylene of high purity is produced by upcycling the xylenes by a method called "C8-aromatics loop", including steps of separation (elimination of the heavy compounds in the "xylenes column", extraction of paraxylene) and isomerization of the xylenes. Extraction of paraxylene of high purity by selective adsorption is well known in the prior art. The technological background describing the production of paraxylene of very high purity is illustrated in the applicant's patent EP-A-531 191, and is based on the separation of paraxylene from a feedstock of aromatic hydrocarbons essentially with 8 carbon atoms in an adsorber by contact with a bed of zeolite adsorbent in the presence of an appropriate desorption solvent (desorbent).

For this type of separation, a family of methods of adsorption and associated devices is used, known as methods or devices for chromatographic separation or "simulated moving bed" or "simulated counter-current", hereinafter referred to as "SMB" methods and devices similar to those described in U.S. Pat. Nos. 2,985,589, 4,402,832 and 4,498,991, and which are applied, among others, to the C8 aromatic cuts.

With this type of process, an extract stream is obtained containing desorbent and essentially paraxylene of high purity, typically above 99.7%, and a raffinate stream containing desorbent, metaxylene, orthoxylene, ethylbenzene, and practically no paraxylene.

The conventional feedstocks of the units for separating xylenes consist of aromatic hydrocarbons with 8 carbon atoms generally originating from catalytic reforming of naphthas (69%) or, to a lesser extent, disproportionation of toluene (27%), and more rarely steam cracking, coking of coal and aromatization of LPGs.

These conventional feedstocks of aromatic hydrocarbons do not contain aromatic oxygen-containing impurities of the phenol type or derivatives thereof.

The desorption solvent may be any desorbent known to a person skilled in the art and having a boiling point below that of the feedstock, such as toluene, but also a desorbent the boiling point of which is above that of the feedstock, such as para-diethylbenzene (PDEB).

Unconventional feedstocks, derived partially or completely from processes for biomass conversion, or from other processes using oxygen-containing substances as raw material, have a high content of oxygen-containing impurities, such as ketones, alcohols and predominantly phenols, said phenols comprising compounds with at least one phenyl group and a hydroxyl group. The predominant oxygen-containing impurities in the unconventional feedstocks are the aromatic oxygen-containing compounds, i.e. compounds comprising at least one aromatic ring and at least one oxygen atom. This last-mentioned family contains in particular phenol and/or its derivatives such as alkyl-phenol (in particular the cresols), alkoxy-benzene (in particular anisole), alkoxy-phenol and biphenol. This family also contains in particular the compounds comprising a phenyl group and a carbonyl group, such as benzaldehyde and acetophenone.

Hereinafter, the term "aromatic oxygen-containing impurities" will be used to denote any combination of compounds comprising at least one aromatic ring and at least one oxygen atom, in particular including the compounds described above.

The biosourced feedstocks containing aromatic oxygen-containing impurities, in particular phenol and/or its derivatives, originate for example from the following processes:

Catalytic cracking of oils from fast pyrolysis (pyrolysis of lignin present in biomass): this is a post-treatment by acid catalysis such as described for example in Adjaye et al., Fuel Processing Technology, 1996 (48) p115.

Catalytic pyrolysis of biomass as described for example in Park et al., Appl. Cat. B: Environmental, 2010, Jackson et al. (J. Anal. Appl. Pyrolysis 85 (2009) 226-230) and Thring et al. (Fuel Proc. Tech. 62 (2000) 17-30).

Alcohol route to butenes to xylenes as described in the patents of DuPont (US2005228203/4) or GEVO (US2009299109).

Feedstocks obtained from other processes using oxygen-containing substances as raw material, containing aromatic oxygen-containing impurities, in particular phenol and/or its derivatives, are obtained for example by methylation of toluene (Exxonmobil U.S. Pat. No. 8,399,727).

The feeds of aromatic hydrocarbons with 8 carbon atoms entering the process for the separation of paraxylene come from the overhead stream of the "xylenes column", a distillation column the role of which is to remove the heaviest compounds, in particular the C9-C10 hydrocarbons. Thus, in the case of unconventional feedstocks, with a high content of aromatic oxygen-containing impurities, in particular phenol and/or its derivatives, this distillation column makes it possible to separate a good proportion of the impurities, in particular the heaviest ones. Consequently, among the aromatic oxygen-containing impurities present in the unconventional feedstocks of aromatic hydrocarbons with 8 carbon atoms, the predominant compound is phenol, its derivatives being present at far lower contents.

In the present application, by phenol and derivatives thereof is meant any type of aromatic oxygen-containing impurities, and by the concentration of these impurities, is meant that said concentration relates to all of the aromatic oxygen-containing impurities.

EXAMINATION OF THE PRIOR ART

Méthivier teaches us (Ind. Eng. Chem. Res. 1998, 37, 604-608) that when oxygen-containing molecules having an aromatic ring, such as acetophenone, benzaldehyde and benzyl alcohol, are present as impurities, this greatly impairs separation of the aromatic C8 isomers by adsorption on the zeolite faujasite. Consequently, a person skilled in the art expects the presence of aromatic oxygen-containing impurities in the feed entering the process for separation by adsorption to lead to irreversible adsorption and a continuous degradation of the performance of the separation process.

Among the aromatic oxygen-containing impurities, phenol, which is the predominant impurity, is a compound that is also particularly problematic because its boiling point, i.e. 182° C., is close to the boiling point of para-diethylbenzene (PDEB), i.e. 184° C., commonly used as desorbent in the process for separation of paraxylene.

In fact, during the distillation of the streams leaving the separation process, i.e. the stream of extract rich in paraxylene and the stream of raffinate depleted of paraxylene, the phenol is expected to leave at the bottom of the column with the PDEB, because they have similar boiling points. The phenol present in the outgoing streams would then be recycled to the adsorber via the injection of desorbent, and would thus tend to accumulate in the adsorption section as the operation proceeds.

To avoid any irreversible adsorption of aromatic oxygen-containing impurities and to avoid accumulation of these impurities in the adsorption section, which would degrade the separation efficiency of the adsorption process, a person skilled in the art recommends preparation of the feedstocks introduced into the process for separation of xylenes, prior to their injection into the adsorber, by a conventional pretreatment step such as hydrotreatment in order to convert the oxygen-containing molecules to $H_2O$.

The $H_2O$ thus formed can be separated from the aromatic molecules by fractionation or by dehydration of the hydrocarbon stream. This catalytic hydrotreatment step will preferably use a hydrodeoxygenation catalyst known from the prior art comprising an inorganic oxide support such as alumina and metals selected from groups VIB (6) and VIII (9-10) of the periodic table.

Alternatively or as a supplement to the hydrotreatment step, the feedstock preparation step may comprise bringing into contact with agents capable of capturing the oxygen-containing molecules present. The content of elemental oxygen recommended is typically similar to that of the specifications for sulphur and for nitrogen, which are generally below 1 ppm by weight.

Moreover, this step of treatment of the feedstock requires setting up on-line monitoring of a very low content of aromatic oxygen-containing impurities in the streams sent to the adsorber.

The use of a feedstock derived partially or completely from processes for biomass conversion, or from other processes using oxygen-containing substances as raw material, therefore requires a priori a complex and expensive step of preparation of this feedstock prior to its injection into the adsorption section.

The present invention describes a solution making it possible to treat feedstocks containing compounds of the phenol type and/or its derivatives, without using a preliminary hydrotreatment unit.

In the context of the present invention, it was observed unexpectedly that the presence of water in the feedstock causes a very significant reduction in the affinity of phenol and of its derivatives for the zeolite faujasite, at least by a factor of 10, or even 100, depending on the concentration of water in the feedstock.

BRIEF DESCRIPTION OF THE INVENTION

The present invention is situated within the field of simulated moving bed (SMB) processes for separation of xylenes. This process usually operates starting from hydrocarbon-containing feedstocks that are mixtures of xylenes originating from refining processes, in particular catalytic reforming of gasolines.

The process according to the present invention treats unconventional feedstocks, which may comprise oxygen-containing compounds of the phenol type and/or derivatives thereof. These unconventional feedstocks, originating partially or completely from processes for biomass conversion, or from other processes using oxygen-containing substances as raw material, have a high content of aromatic oxygen-containing impurities. The present invention describes a simple adaptation of the SMB process for separating xylenes, enabling it to treat the aforesaid unconventional feedstocks, without using an expensive unit for hydrotreatment of these feedstocks.

Hereinafter, all ppm values are ppm by weight.

The present invention may briefly be described as a process for separating paraxylene by simulated moving bed (SMB) chromatography starting from a feed F essentially comprising paraxylene and the aromatic C8 isomers thereof as well as aromatic oxygen-containing impurities, including phenol and/or derivatives thereof, at a concentration between 0.1 ppm by weight and 50 ppm by weight, said process comprising a step of adsorption on an adsorbent based on the zeolite faujasite and a step of desorption of the isomers from the mixture by means of a desorbent, delivering an extract rich in paraxylene and at least one raffinate containing ethylbenzene, orthoxylene, metaxylene and a very small quantity of paraxylene, said process being characterized in that a quantity of water is introduced in the ingoing streams (entirely in the feed, entirely in the desorbent, or partly in the feed and partly in the desorbent) such that the weighted average of the water content measured in these ingoing streams is greater than the cumulative contents of aromatic oxygen-containing impurities in these same ingoing streams, while remaining below 200 ppm by weight.

"Introduction of water in the ingoing streams" covers the three cases: either introduction solely in the feed, or introduction solely in the desorbent, or introduction partly in the feed and partly in the desorbent.

More precisely, the process for separating paraxylene by simulated moving bed (SMB) chromatography according to the present invention is characterized by a water content introduced in the ingoing streams (feed and desorbent) that satisfies the two conditions:
(1) [water]/[aromatic oxygen-containing substances] greater than 10
(2) [water]/[aromatic oxygen-containing substances] less than 200
(3) [water] less than 200 ppm, and preferably less than 150 ppm the smaller of the two values obtained by conditions (2) and (3) effectively being the value adopted.

The concentration [aromatic oxygen-containing substances] is to be understood as the cumulative content of aromatic oxygen-containing impurities in the ingoing streams.

A person skilled in the art expects the presence of water at low content in the feed to cause a partial reduction in the quantity of phenol and of its derivatives adsorbed in the zeolite faujasite, owing to the competition inherent in the adsorption of several compounds. The reduction in the adsorption of the compounds is generally in proportion to their concentration and their affinity for the adsorbent.

It was observed, unexpectedly, that the presence of water in the feed reduces the affinity of phenol and of its derivatives for the zeolite faujasite very significantly, at least by a factor of 10, or even 100, depending on the concentration of water in the feed.

The process according to the present invention may be carried out in one or more units of the SMB type, each unit having a number of beds that may be up to 24.

Preferably, the process for separating paraxylene by simulated moving bed (SMB) chromatography according to the invention comprises at least one unit of 24 beds of adsorbent with division into zones defined as follows:
Zone 1=zone of desorption of the required product (here, paraxylene contained in the extract) comprised between the injection of the desorbent D and the withdrawal of the extract E;

Zone 2=zone of desorption of the compounds of the raffinate, comprised between the withdrawal of the extract E and the injection of the feed to be fractionated F;

Zone 3=zone of adsorption of the required product (paraxylene), comprised between the injection of the feed and the withdrawal of the raffinate R; and Zone 4=zone located between the withdrawal of the raffinate and the injection of the desorbent.

The separation process in an SMB device therefore operates according to a configuration (a, b, c, d) with:
 a=number of beds of adsorbent operating in zone 1;
 b=number of beds of adsorbent operating in zone 2;
 c=number of beds of adsorbent operating in zone 3;
 d=number of beds of adsorbent operating in zone 4,
and preferably a=5; b=9; c=7; d=3, or a=4; b=10; c=7; d=3, or a=5; b=8; c=8; d=3.

Also preferably, the process for separating paraxylene by simulated moving bed (SMB) chromatography according to the present invention comprises at least one unit of 15 beds of adsorbent, with division into zones defined as follows:

Zone 1=zone of desorption of the required product (here, paraxylene contained in the extract) comprised between the injection of the desorbent D and the withdrawal of the extract E;

Zone 2=zone of desorption of the compounds of the raffinate, comprised between the withdrawal of the extract E and the injection of the feed to be fractionated F;

Zone 3=zone of adsorption of the required product (paraxylene), comprised between the injection of the feed and the withdrawal of the raffinate R; and Zone 4=zone located between the withdrawal of the raffinate and the injection of the desorbent.

The separation process in an SMB device therefore operates according to a configuration (a, b, c, d) with:
 a=number of beds of adsorbent operating in zone 1;
 b=number of beds of adsorbent operating in zone 2;
 c=number of beds of adsorbent operating in zone 3;
 d=number of beds of adsorbent operating in zone 4, and preferably a=3; b=6; c=4; d=2 or a=3; b=5; c=5; d=2.

DETAILED DESCRIPTION OF THE INVENTION

The present invention relates to a process for separating paraxylene by simulated moving bed (SMB) chromatography starting from a feed F essentially comprising paraxylene and the aromatic C8 isomers thereof as well as aromatic oxygen-containing impurities, including phenol and/or derivatives thereof, said process comprising a step of adsorption on an adsorbent based on the zeolite faujasite and a step of desorption of the isomers from the mixture by means of a desorbent, delivering an extract rich in paraxylene and at least one raffinate containing ethylbenzene, orthoxylene, metaxylene and a very small quantity of paraxylene.

SMB chromatographic separation is well known in the state of the art.

As a general rule, a simulated moving bed comprises at least three chromatographic zones, optionally four or five, each of these zones consisting of at least one bed, and a portion of column called a zone is comprised between two successive points of supply and withdrawal.

Typically, at least one feed F to be fractionated and a desorbent (sometimes called eluent) are fed in and at least one raffinate R and an extract E are withdrawn.

The points of supply and withdrawal are modified over the course of time, typically displaced towards the bottom of a bed, in a synchronized manner.

By definition, each of the operating zones is denoted by a number:

Zone 1=zone of desorption of the required product (here, paraxylene contained in the extract) comprised between the injection of the desorbent D and the withdrawal of the extract E;

Zone 2=zone of desorption of the compounds of the raffinate, comprised between the withdrawal of the extract E and the injection of the feed to be fractionated F;

Zone 3=zone of adsorption of the required product (paraxylene), comprised between the injection of the feed and the withdrawal of the raffinate R; and Zone 4=zone located between the withdrawal of the raffinate and the injection of the desorbent.

The separation process in an SMB device therefore operates according to a configuration (a, b, c, d) with:
 a=number of beds of adsorbent operating in zone 1;
 b=number of beds of adsorbent operating in zone 2;
 c=number of beds of adsorbent operating in zone 3;
 d=number of beds of adsorbent operating in zone 4.

For the units comprising 24 beds, preferably a=5; b=9; c=7; d=3, or
 a=4; b=10; c=7; d=3 or
 a=5; b=8; c=8; d=3.

For the units comprising 15 beds, preferably a=3; b=6; c=4; d=2 or a=3; b=5; c=5; d=2.

According to a variant of the simulated moving bed (SMB) separating unit, two distilled raffinates R1 and R2 of different compositions may also be produced. R1 is the "first raffinate", or "intermediate raffinate", and R2 is the second raffinate.

In this case the SMB separating unit then comprises an increased number of operating zones delimited by the injections of the feed, of the desorbent, and the withdrawals of an extract containing the required product, of an intermediate raffinate (or first raffinate), and of a second raffinate. The two raffinates have different compositions. For example, for separating an aromatic C8 cut, in which the extract is the required product, the first raffinate (or intermediate raffinate) is typically relatively rich in ethylbenzene and relatively depleted of orthoxylene and metaxylene, whereas the second raffinate is on the contrary relatively depleted of ethylbenzene and relatively rich in orthoxylene and metaxylene. According to this variant, zones 1, 2 and 4 are not modified. However, zone 3 is divided into a zone 3A and a zone 3B, i.e.:

zone 3A of adsorption of the required product, comprised between the injection of the feed and the withdrawal of the intermediate raffinate;

zone 3B of adsorption of the main product of the intermediate raffinate, comprised between the withdrawal of the intermediate raffinate and the withdrawal of the second raffinate.

According to the invention, zone 3A and zone 3B are regarded as forming part of the same zone 3.

The SMB devices typically comprise at least one column (and often two), containing the beds of adsorbent, separated by plates with chamber(s) for distribution and/or extraction of fluids into or from the different beds of adsorbent, and controlled means for sequential distribution and extraction of fluids.

These controlled means for distribution and extraction of fluids of an SMB are typically of one of the following two main types of technology:

either, for each plate, a plurality of controlled on/off valves for supply or withdrawal of the fluids, these valves typically being located in the immediate vicinity of the corresponding plate, and comprising for each plate Pi at least 4 controlled on/off two-way valves respectively for supply of the fluids F and D and for withdrawal of the fluids E and R.

or a multi-way rotary valve for supply or withdrawal of the fluids on all of the plates.

The separation of paraxylene from aromatic cuts is typically carried out in two ways:

In a first route, called "hybrid route", SMB separation is carried out, giving PX of low purity, for example 95%, which is then purified by crystallization to obtain PX of high purity, typically a commercial purity of 99.7% or more.

In a second route, called "stand alone" (direct), SMB separation is carried out, giving PX of high purity directly, typically of 99.7% or more. This process also allows a raffinate to be obtained that is rich in ethylbenzene, orthoxylene and metaxylene, which is often recycled to the SMB after isomerization.

The commercial SMB units of this type generally operate with 24 beds of adsorbent, in order to obtain PX of the desired high purity, above 99.5% and typically of at least 99.7 wt %, or at least to obtain this purity with a yield of PX above 97%.

Carrying out separation with a unit operating with a smaller number of beds of adsorbent, for example 15 beds, is still within the scope of the invention.

An SMB separating unit of this kind is generally operated at a temperature comprised between 20° C. and 250° C., preferably between 90° C. and 210° C., and more preferably between 160° C. and 200° C., and at a pressure comprised between the bubble-point pressure of the xylenes at the operating temperature and 2 MPa.

The desorbent used in the SMB unit is generally selected from para-diethylbenzene (or PDEB), toluene, para-difluorobenzene or mixed diethylbenzenes.

The volume ratio of desorbent to feed in the SMB unit is typically comprised between 0.5 and 2.5 and preferably comprised between 1.05 and 1.7.

The streams of raffinate and of extract are each introduced into a distillation column, in order to separate the desorbent, which is recycled to the SMB unit, from the compounds with 8 carbon atoms.

When it is desired to maintain a known water content in the ingoing streams, two controlled flows of desorbent are injected, one of anhydrous product, the other of water-saturated product and a controlled flow of anhydrous feed (the opposite may also be carried out).

To measure the water contents of the ingoing and outgoing streams, the KARL FISCHER method is used for contents above 15 ppm.

When these contents are below 15 ppm, reliance is placed on the in-line measurements supplied by the in-line analysis probes (PANAMETRIC apparatus, series 1).

Calibration is performed between 15 ppm and 200 ppm. Extrapolation of this calibration curve to contents between 1 and 15 ppm is regarded as valid.

The cumulative contents of aromatic oxygen-containing impurities in the ingoing streams (feed and/or desorbent) are between 0.1 ppm and 50 ppm (all contents expressed in ppm are ppm by weight).

A quantity of water is introduced into the ingoing streams (feed and/or desorbent) such that the weighted average of the water contents measured in these ingoing streams is greater than the cumulative contents of aromatic oxygen-containing impurities in these same ingoing streams.

Using F1 to denote the feed stream, and F2 the desorbent stream, C the concentration of water in the feed and C2 the concentration of water in the desorbent, $C^*1$ the cumulative content of aromatic oxygen-containing impurities in the feed and $C^*2$ the cumulative content of aromatic oxygen-containing impurities in the desorbent, it is noted that:

concentration of water in the ingoing streams=[water]
=C1F1+C2F2/(F1+F2)

cumulative content of aromatic oxygen-containing impurities in the ingoing streams=[aromatic oxygen-containing substances]=$C^*1F1+C^*2F2$/(F1+F2)

Preferably, the water content defined above is greater than 10 times the content of aromatic oxygen-containing impurities.

Preferably again, the water content defined above is less than 200 times the content of aromatic oxygen-containing impurities.

However, there is an absolute upper limit to the water content introduced into the ingoing streams, which is 200 ppm and preferably 150 ppm.

The expression for these two conditions is therefore written:

(1) [water]/[aromatic oxygen-containing substances] greater than 10

(2) [water]/[aromatic oxygen-containing substances] less than 200

(3) [water] less than 200 ppm, and preferably less than 150 ppm.

Compatibility between conditions (2) and (3) is ensured by taking the smaller of the two values (2) or (3).

The injection of a controlled quantity of water into the adsorber greater than the quantity of oxygen-containing aromatic impurities makes it possible to avoid high adsorption of the latter, thus avoiding degradation of the performance of the adsorption process connected with the presence of these oxygen-containing compounds at inlet.

The injection of water may either be carried out in the feed, or in the desorbent, or partly in the feed and partly in the desorbent.

The expression injection of water in the feed and/or the desorbent covers all of these instances.

The injection of water can be carried out continuously or separately at certain time intervals. When said injection is performed separately, the inequalities (1), (2) and (3) are to be respected on average for a duration of one month.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 13/59.083, filed Sep. 20, 2013, are incorporated by reference herein.

EXAMPLES

Example 1 (Not According to the Invention).
Adsorption of Phenol from a Phenol/Paraxylene Feed on Zeolite BaX in the Absence of Water In this example, a drilling test was carried out by frontal chromatography to evaluate the adsorption of phenol from a phenol/paraxylene feed on zeolite BaX in the absence of water.

A quantity of 1.89 g of an anhydrous BaX adsorbent is put in a column with length of 4.85 cm and inside diameter of 0.78 cm. For the test, column temperature is maintained at 175° C., and the pressure is sufficient to maintain the liquid phase.

The effluent from the column is sampled (60 samples) and then analysed by gas phase chromatography to determine the composition of the effluent at different time intervals. The feed consists of pure paraxylene with addition of 10 ppm of phenol.

The procedure used is as follows:
Filling the column with the adsorbent and setting-up in the test bench.
Gradual increase to 175° C. under toluene stream (5 cm$^3$/min).
Switching from solvent to feed for injecting the feed (5 cm$^3$/min). Injection of the feed is then maintained for a sufficient time to reach thermodynamic equilibrium.
Collection and analysis of the effluent.

The fraction of the capacity of the adsorbent occupied by phenol at the end of the experiment is 2.9%.

This example clearly shows that in the absence of water, phenol is adsorbed very strongly on zeolite BaX, which leads to a significant reduction in the capacity of the adsorbent.

Example 2. Adsorption of Phenol from a Phenol/Paraxylene Feed on Zeolite BaX with Co-injection of Water (Laboratory Experiment)

Example 1 is reproduced using an adsorbent based on zeolite BaX the water content of which is 5.4 wt % (in order to reproduce an adsorbent at equilibrium with a feed of C8-aromatics with addition of 90 ppm of water at 175° C.) and with a feed composed of pure paraxylene with addition of 10 ppm of phenol and 90 ppm of water, i.e. a water/phenol ratio of 9.0.

Calculation of the quantities adsorbed at the end of the test shows that the fraction of the capacity of the adsorbent occupied by phenol at the end of the experiment is then 0.13%.

The presence of water in the feed therefore greatly reduces the adsorption of phenol on the adsorbent. This effect is unexpected, as a person skilled in the art might expect that phenol, even in the presence of water, would continue to be adsorbed on the zeolite.

Example 3 (Process According to the Invention)

Paraxylene is separated from a feed of aromatics with 8 carbon atoms on a simulated moving bed device equipped with 24 beds of adsorbent and using toluene as desorbent.

This simulated moving bed device comprises 24 beds of adsorbent with a height of 1.1 m and an internal section of 3.5×10$^{-4}$ m$^2$, with the injection of feed, injection of desorbent, withdrawal of extract and withdrawal of raffinate.

The configuration used is 5/9/7/3, i.e.:
5 beds in zone 1;
9 beds in zone 2;
7 beds in zone 3;
3 beds in zone 4.

The adsorbent used is a zeolite of the BaX type, and the desorbent is toluene.

The degree of hydration of the adsorbent is 5.4 wt %. The temperature is 175° C., and the pressure is 1.5 MPa.

The feed F is made up of 20% of PX, 22% of OX, 48% of MX, 5% of EB, 8 ppm of phenol and 90 ppm of water, i.e. a water/phenol ratio of 11.25.

The switching time used is 35 seconds. The flow rates of liquid in the different zones are as follows:
9.60 cm$^3$·s$^{-1}$ in zone 1;
7.93 cm$^3$·s$^{-1}$ in zone 2;
10.42 cm$^3$·s$^{-1}$ in zone 3;
6.57 cm$^3$·s$^{-1}$ in zone 4.

In order to determine any deterioration of performance connected with irreversible adsorption of phenol, the performance is monitored as a function of time.

After initial setting (t=2 days), a purity of PX is obtained in the extract of 99.84 wt % and a yield of PX (ratio of the quantity of paraxylene leaving in the extract to the quantity of paraxylene injected with the feed) of 97.15 wt %.

The performance at the end of the test (t=45 days) is as follows: purity of PX in the extract of 99.82 wt % and a yield of PX (ratio of the quantity of paraxylene leaving in the extract to the quantity of paraxylene injected with the feed) of 97.25 wt %.

Therefore no significant deterioration in performance of the process is found during the test.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A method for reducing the affinity of phenol and/or of its derivatives for the zeolite faujasite in a process for separating paraxylene by simulated moving bed (SMB) chromatography from a feed F comprising paraxylene and aromatic C8 isomers thereof as well as oxygen-containing aromatic impurities, including phenol and/or derivatives thereof, at a concentration between 0.1 ppm by weight and 50 ppm by weight, said process comprising a step of adsorption on an adsorbent based on the zeolite faujasite and a step of desorption of the aromatic C8 isomers by a desorbent, delivering an extract rich in paraxylene and at least one raffinate containing ethylbenzene, orthoxylene, metaxylene and a lesser quantity of paraxylene, wherein the method comprises introducing a quantity of water into the feed, such that the weighted average of water content measured in the feed is greater than the cumulative contents of oxygen-containing aromatic impurities in said feed, while remaining below 200 ppm by weight, and
wherein the feed comprises water and phenol in a water to phenol weight ratio range of 9.0-11.25.

2. The method for reducing the affinity of phenol and/or of its derivatives for the zeolite faujasite according to claim 1, in which the water content introduced into the feed only, satisfies the two conditions:

[water]/[oxygen-containing aromatic substances] greater than 10

[water]/[oxygen-containing aromatic substances] less than 200.

3. The method for reducing the affinity of phenol and/or of its derivatives for the zeolite faujasite according to claim 1, wherein the process operates at a temperature between 20° C. and 250° C., and at a pressure between the bubble-point pressure of the xylenes at the temperature and 2 MPa.

4. The method for reducing the affinity of phenol and/or of its derivatives for the zeolite faujasite according to claim 1, wherein the process is performed in at least one unit of 24 beds of adsorbent and with division into zones defined as follows:

Zone 1=zone of desorption of required product, which is the paraxylene contained in the extract, comprised between injection of the desorbent D and withdrawal of the extract E;

Zone 2=zone of desorption of compounds of the raffinate, comprised between the withdrawal of the extract E and injection of the feed F to be fractionated;

Zone 3=zone of adsorption of the required product, which is paraxylene, comprised between the injection of the feed and withdrawal of the raffinate R; and Zone 4=zone located between the withdrawal of the raffinate and the injection of the desorbent.

5. The method for reducing the affinity of phenol and/or of its derivatives for the zeolite faujasite according to claim 1, wherein the process is performed in at least one unit of 15 beds of adsorbent, and with division into zones defined as follows:

Zone 1=zone of desorption of required product paraxylene contained in the extract, comprised between injection of the desorbent D and withdrawal of the extract E;

Zone 2=zone of desorption of compounds of the raffinate, comprised between the withdrawal of the extract E and injection of the feed F to be fractionated;

Zone 3=zone of adsorption of the required product, which is paraxylene, comprised between the injection of the feed and withdrawal of the raffinate R, and Zone 4=zone located between the withdrawal of the raffinate and the injection of the desorbent.

6. The method for reducing the affinity of phenol and/or of its derivatives for the zeolite faujasite according to claim 1, wherein the process is performed in at least one unit of 24 beds of adsorbent and with division into zones defined as follows:

Zone 1=zone of desorption of required product, which is the paraxylene contained in the extract, comprised between injection of the desorbent D and withdrawal of the extract E;

Zone 2=zone of desorption of compounds of the raffinate, comprised between the withdrawal of the extract E and injection of the feed F to be fractionated;

Zone 3=zone of adsorption of the required product, which is paraxylene, comprised between the injection of the feed and withdrawal of the raffinate R; and Zone 4=zone located between the withdrawal of the raffinate and the injection of the desorbent, wherein the separation process in an SMB device therefore operates according to a configuration (a, b, c, d) with:

a=number of beds of adsorbent operating in Zone 1;
b=number of beds of adsorbent operating in Zone 2;
c=number of beds of adsorbent operating in Zone 3;
d=number of beds of adsorbent operating in Zone 4,
wherein a=5; b=9; c=7; d=3, or a=4; b=10; c=7; d=3, or a=5; b=8; c=8; d=3.

7. The method for reducing the affinity of phenol and/or of its derivatives for the zeolite faujasite according to claim 1, wherein the process is performed in at least one unit of 15 beds of adsorbent, and with division into zones defined as follows:

Zone 1=zone of desorption of required product paraxylene contained in the extract, comprised between injection of the desorbent D and withdrawal of the extract E;

Zone 2=zone of desorption of compounds of the raffinate, comprised between the withdrawal of the extract E and injection of the feed F to be fractionated;

Zone 3=zone of adsorption of the required product, which is paraxylene, comprised between the injection of the feed and withdrawal of the raffinate R, and Zone 4=zone located between the withdrawal of the raffinate and the injection of the desorbent, wherein the separation process in an SMB device therefore operates according to a configuration (a, b, c, d) with:

a=number of beds of adsorbent operating in Zone 1;
b=number of beds of adsorbent operating in Zone 2;
c=number of beds of adsorbent operating in Zone 3;
d=number of beds of adsorbent operating in Zone 4,
wherein a=3; b=6; c=4; d=2 or a=3; b=5; c=5; d=2.

8. The method for reducing the affinity of phenol and/or of its derivatives for the zeolite faujasite according to claim 1, in which the weighted average of water content measured in the feed is greater than the cumulative contents of oxygen-containing aromatic impurities in the feed, while remaining below 150 ppm by weight.

9. The method for reducing the affinity of phenol and/or of its derivatives for the zeolite faujasite according to claim 1, wherein the process operates at a temperature between 90° C. and 210° C., and at a pressure between the bubble-point pressure of the xylenes at the temperature and 2 MPa.

10. The method for reducing the affinity of phenol and/or of its derivatives for the zeolite faujasite according to claim 1, wherein the process operates at a temperature between 160° C. and 200° C., and at a pressure between the bubble-point pressure of the xylenes at the temperature and 2 MPa.

11. A method for reducing affinity of phenol and/or of its derivatives for a zeolite faujasite in a process for separating paraxylene by simulated moving bed (SMB) chromatography from a feed comprising phenol and/or of its derivatives, the method comprising:

adding water such that a water content measured in an ingoing stream of feed which contacts the zeolite faujasite is greater than a cumulative contents of oxygen-containing aromatic impurities in the same ingoing stream of feed, while remaining below 200 ppm by weight, and wherein water and phenol are in a water to phenol weight ratio range of 9.0-11.25, and wherein the feed comprises paraxylene and aromatic C8 isomers thereof as well as oxygen-containing aromatic impurities, including phenol and/or derivatives thereof, at a concentration between 0.1 ppm by weight and 50 ppm by weight.

12. A method for reducing the affinity of phenol and/or of its derivatives for the zeolite faujasite according to claim 11, wherein the water content measured in the ingoing stream of feed is greater than the cumulative contents of oxygen-containing aromatic impurities in the same ingoing stream of feed, while remaining below 150 ppm by weight.

* * * * *